US00PP22710P2

(12) United States Plant Patent
Hall

(10) Patent No.: US PP22,710 P2
(45) Date of Patent: May 1, 2012

(54) LAVENDER PLANT NAMED 'MYRLEIGH'

(50) Latin Name: *Lavandula stoechas*
Varietal Denomination: Myrleigh

(76) Inventor: Elsie Kazerine Hall, Wairau Valley (NZ)

( * ) Notice: Subject to any disclaimer, the term of this patent is extended or adjusted under 35 U.S.C. 154(b) by 0 days.

(21) Appl. No.: 12/807,661

(22) Filed: Sep. 10, 2010

(51) Int. Cl.
*A01H 5/00* (2006.01)

(52) U.S. Cl. ..... Plt./445

(58) Field of Classification Search ..... Plt./445
See application file for complete search history.

(56) References Cited

OTHER PUBLICATIONS

GTITM UPOVROM Citation for 'Myrleigh' as per NZ PBR LAV029; Sep. 4, 2002.*

* cited by examiner

*Primary Examiner* — Kent L Bell
(74) *Attorney, Agent, or Firm* — Mark Bourgeois

(57) ABSTRACT

A new cultivar of Lavender plant named 'Myrleigh' that is characterized by violet flowers, light violet sterile bracts, flowers having a musk fragrance and grey-green foliage.

1 Drawing Sheet

Botanical classification: *Lavandula stoechas.*
Variety denomination: 'Myrleigh'.

BACKGROUND OF THE INVENTION

The present invention relates to a new and distinct cultivar of Lavender plant botanically known as *Lavandula stoechas* and hereinafter referred to by the cultivar name 'Myrleigh'.

The new cultivar was discovered in 1999 as a single plant in a bed of *Lavandula stoechas* plants in a cultivated area of Wairau Valley, New Zealand. The exact parent plants are unknown.

Asexual reproduction of the new cultivar 'Myrleigh' by terminal cuttings was first performed in 2002 in Wairau Valley, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new Lavender cultivar 'Myrleigh'. These traits in combination distinguish 'Myrleigh' as a new and distinct cultivar.

1. Lavender 'Myrleigh' exhibits violet flowers with light violet sterile bracts.
2. Lavender 'Myrleigh' exhibits flowers having a musk fragrance.
3. Lavender 'Myrleigh' exhibits grey-green foliage.

The closest comparison varieties are Lavender 'Marshwood' (not patented) and Lavender 'Major' (not patented).

'Myrleigh' is different than 'Marshwood' in having flowers that have smaller petals, darker colored petals, smaller terminal bracts, darker colored terminal bracts and gray-green leaves. The leaves of 'Marshwood' are green.

'Myrleigh' is different than 'Major' in having flowers that have lighter colored terminal bracts and violet petals. The petals of 'Major' are blue-pink.

BRIEF DESCRIPTION OF THE DRAWING

The accompanying photograph illustrates the distinguishing traits of Lavender 'Myrleigh'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new Lavender cultivar named 'Myrleigh'. Data was collected in Wairau Valley, New Zealand from 12 month old field grown plants. The time of year was Summer and the average temperature was 20 to 32° Centigrade during the day and 9 to 18° Centigrade at night. Color determinations are in accordance with The Royal Horticultural Society Colour Chart 2001 edition, except where general color terms of ordinary dictionary significance are used. The growing requirements are similar to the species. 'Myrleigh' has not been tested under all possible conditions and phenotypic differences may be observed with variations in environmental, climatic, and cultural conditions, however, without any variance in genotype.

Botanical classification: *Lavandula stoechas* 'Myrleigh'.
Use: Ornamental perennial.
Parentage: The exact parent plants of 'Myrleigh' are unknown.
Vigor: Moderate.
Container size: 9 cm. and larger.
Growth habit: Upright, outwardly spreading.
Plant shape: Rounded with erect flower spikes.
Height: Average 30 cm. in height.
Width: Average 60 cm. in width.
Hardiness: −9° to 38° C.
Propagation: Terminal cuttings.
Crop time: 9 months.
Stem:
*Branching habit.*—Free branching.
*Number of lateral branches.*—Approximately 50.
*Lateral branch diameter.*—3 mm. in diameter.
*Lateral branch length.*—25 cm. in length.
*Lateral branch strength.*—Strong.
*Color.*—195C.

*Pubescence*.—Lightly covered with short hairs.
*Internode length*.—3 cm. between nodes.
*Shape*.—Round.

Foliage:
*Leaf arrangement*.—Opposite.
*Compound or single*.—Single.
*Quantity of leaves per lateral branch*.—22.
*Leaf shape*.—Linear.
*Leaf apex*.—Acute.
*Leaf base*.—Rounded.
*Leaf length*.—4.0 cm. in length.
*Leaf width*.—5.0 mm. in width.
*Texture*.—Velvety.
*Pubescence*.—Present.
*Leaf margin*.—Entire.
*Vein pattern*.—Pinnate.
*Young leaf color* (*upper surface*).—191D.
*Young leaf color* (*lower surface*).—191D.
*Mature leaf color* (*upper surface*).—191B.
*Mature leaf color* (*lower surface*).—191C.
*Vein color* (*both surfaces*).—191B.
*Leaf attachment*.—Sessile.

Flower:
*Flower arrangement*.—Terminal cylindrical spikes.
*Inflorescence dimensions*.—4.0 cm. in length and 1.5 cm. in diameter.
*Quantity of flowers and buds per inflorescence*.—Approximately 50.
*Quantity of inflorescences per plant*.—Approximately 182.
*Flowering season*.—Spring to Summer.
*Time to flower or response time*.—4 to 6 weeks after buds form.
*Fragrance*.—Musk scent.
*Self-cleaning or persistent*.—Self cleaning.
*Flower bud length*.—27 mm. in length.
*Flower bud diameter*.—13 mm. in diameter.
*Flower bud shape*.—Ovate.
*Bud color*.—83A.
*Flower aspect*.—Outward.
*Flower shape*.—Salverform.
*Flower dimensions*.—4 mm. in diameter and 8 mm. in height.
*Flower longevity*.—Lasts approximately 20 to 25 days.
*Petal arrangement*.—Rotate with five petals fused into a tube.
*Petal shape*.—Spathulate.
*Petal margin*.—Entire.
*Petal apex*.—Rounded.
*Petal Texture*.—Smooth.
*Petal dimensions*.—8 mm. in length and 3 mm. in width.
*Petal color when opening* (*upper side*).—90A.
*Petal color when opening* (*under side*).—90B.
*Petal color when fully opened* (*upper side*).—90A.
*Petal color when fully opened* (*under side*).—90B.
*Petal color fading to*.—90A.

Sepals:
*Sepal number*.—5.
*Sepal shape*.—Linear.
*Sepal apex*.—Acute.
*Sepal base*.—Fused.
*Sepal margin*.—Entire.
*Sepal texture* (*both surfaces*).—Velvety.
*Sepal dimensions*.—3 mm. in length and 1 mm. in width.
*Sepal color* (*both surfaces*).—144C.

Calyx:
*Calyx shape*.—Campanulate tube.
*Calyx dimensions*.—3 mm. in length and 1.5 mm. in diameter.

Peduncle:
*Peduncle dimensions*.—28 cm. in length and 2 mm. in diameter.
*Peduncle angle*.—Vertical.
*Peduncle color*.—N187D.
*Peduncle strength*.—Medium.

Sterile bracts:
*Sterile bract location*.—On top of each spike.
*Sterile bract quantity*.—6.
*Sterile bract shape*.—Oblanceolate.
*Sterile bract apex*.—Rounded.
*Sterile bract base*.—Cuneate.
*Sterile bract margin*.—Entire, undulating.
*Sterile bract texture* (*both surfaces*).—Velvety.
*Sterile bract dimensions*.—6 cm. in length and 40 mm. in width.
*Sterile bract color* (*upper side*).—N82A and N82C.
*Sterile bract color* (*under side*).—N82A and N82C.

Fertile bracts:
*Fertile bract location*.—At the base of each flower.
*Fertile bract shape*.—Obovate.
*Fertile bract apex*.—Acute.
*Fertile bract base*.—Cuneate.
*Fertile bract margin*.—Entire.
*Fertile bract texture* (*both surfaces*).—Velvety.
*Fertile bract dimensions*.—10 mm. in length and 8 mm. in width.
*Fertile bract color* (*upper side*).—79C.
*Fertile bract color* (*under side*).—79C, base 193C.

Reproductive organs:
*Stamen number*.—4.
*Anther shape*.—Dorsifixed, kidney shaped.
*Anther length*.—0.3 mm.
*Amount of pollen*.—Moderate.
*Pistil number*.—1.
*Pistil length*.—2.5 mm.
*Stigma shape*.—Club shaped.
*Style length*.—2.5 mm.
*Ovary color*.—144C.

Fruit and seed production: Plants of the new Lavender have not been observed for fruit and seed production.

Disease and pest resistance: Plants of the new Lavender have not been observed for disease or pest resistance.

What is claimed is:

1. A new and distinct variety of Lavender plant named 'Myrleigh' as described and illustrated.

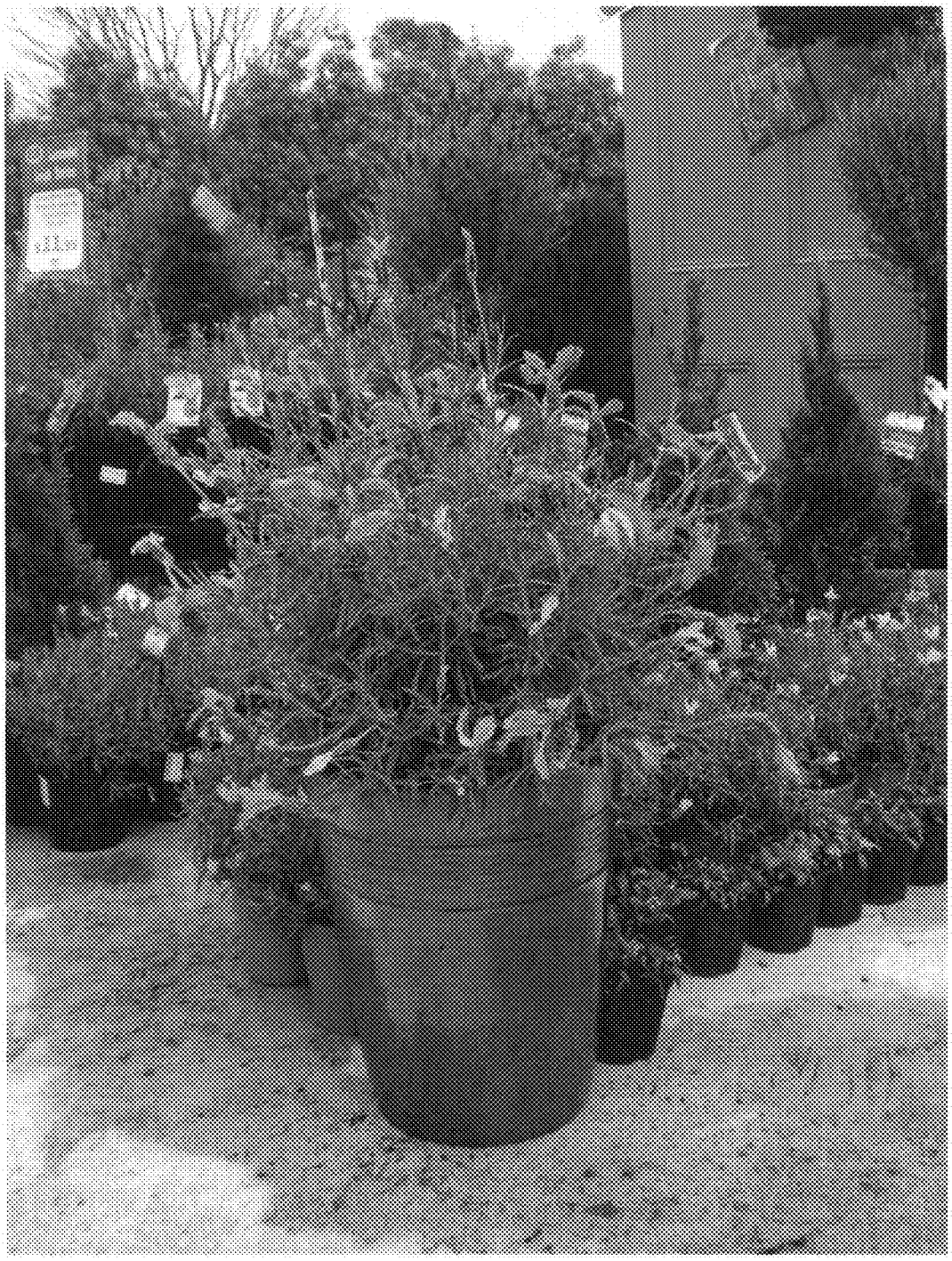

* * * * *